United States Patent [19]
Piper

[11] Patent Number: 6,067,984
[45] Date of Patent: *May 30, 2000

[54] PULMONARY MODULATOR APPARATUS

[76] Inventor: Samuel David Piper, 3929 Arderly Ct., Sacramento, Calif. 95826

[ * ] Notice: This patent issued on a continued prosecution application filed under 37 CFR 1.53(d), and is subject to the twenty year patent term provisions of 35 U.S.C. 154(a)(2).

[21] Appl. No.: 08/949,894

[22] Filed: Oct. 14, 1997

[51] Int. Cl.⁷ ........................................................ A62B 9/02
[52] U.S. Cl. ................................ 128/205.24; 128/204.18
[58] Field of Search .................... 128/205.24, 204.18, 128/204.23

[56] References Cited

U.S. PATENT DOCUMENTS

| | | |
|---|---|---|
| 2,774,346 | 12/1956 | Halliburton . |
| 2,904,035 | 9/1959 | Andreasen . |
| 3,068,856 | 12/1962 | Bird et al. . |
| 3,191,596 | 6/1965 | Bird et al. . |
| 3,653,379 | 4/1972 | Glenn . |
| 3,753,436 | 8/1973 | Bird et al. . |
| 3,916,888 | 11/1975 | Buck et al. . |
| 3,916,890 | 11/1975 | Freeman . |
| 3,918,447 | 11/1975 | Inkster et al. . |
| 3,974,828 | 8/1976 | Bird . |
| 3,976,065 | 8/1976 | Durkan ............................. 128/204.24 |
| 4,022,202 | 5/1977 | Price . |
| 4,039,139 | 8/1977 | Bird . |
| 4,197,843 | 4/1980 | Bird ................................. 128/204.25 |
| 4,429,688 | 2/1984 | Duffy . |
| 4,436,090 | 3/1984 | Darling . |
| 4,502,481 | 3/1985 | Christian . |
| 4,592,349 | 6/1986 | Bird . |
| 4,646,733 | 3/1987 | Stroh et al. . |
| 4,823,828 | 4/1989 | McGinnis . |
| 5,007,420 | 4/1991 | Bird . |
| 5,014,694 | 5/1991 | DeVries . |
| 5,116,088 | 5/1992 | Bird . |
| 5,127,400 | 7/1992 | DeVries et al. .................... 128/204.23 |
| 5,165,398 | 11/1992 | Bird . |
| 5,199,426 | 4/1993 | Aldworth et al. . |
| 5,230,330 | 7/1993 | Price . |
| 5,275,153 | 1/1994 | Kay . |
| 5,307,794 | 5/1994 | Rauterkus et al. . |
| 5,400,779 | 3/1995 | De Resende . |
| 5,423,313 | 6/1995 | Olsson et al. . |
| 5,425,358 | 6/1995 | McGrail et al. . |
| 5,443,062 | 8/1995 | Hayes . |
| 5,460,175 | 10/1995 | Foote et al. . |
| 5,555,880 | 9/1996 | Winter et al. . |
| 5,564,416 | 10/1996 | Jones . |
| 5,572,993 | 11/1996 | Kurome et al. . |
| 5,590,407 | 12/1996 | Schuler . |

FOREIGN PATENT DOCUMENTS

2 170 409   8/1986   United Kingdom .

*Primary Examiner*—Aaron J. Lewis
*Assistant Examiner*—Teena Mitchell
*Attorney, Agent, or Firm*—John P. O'Banion

[57] ABSTRACT

A dual area pressure pulmonary modulator apparatus which provides constant flow, pressure cycled ventilatory support to patients. The pressure pulmonary modulator apparatus opens at a selected pressure and shuts at a substantially lower pressure. The pressure pulmonary modulator apparatus can be incorporated into an automatic resuscitator suited for providing ventilatory support during resuscitation and/or transport of patients. The automatic resuscitator may be combined with a nebulizer to serve as a positive pressure aerosol therapy device. The pressure pulmonary modulator apparatus can also be incorporated into a percussive therapy device used for the mobilization of mucus in patients. The pressure pulmonary modulator apparatus may be made almost entirely of injection molded plastic and is inexpensive, portable and disposable.

37 Claims, 10 Drawing Sheets

PULMONARY MODULATOR APPARATUS

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

1. Field of the Invention

This invention pertains generally to respiratory ventilation devices, and more particularly to a constant flow pulmonary modulator which can be adapted to a number of applications including (1) a respiratory device used for the automatic resuscitation and transport of patients, (2) a positive pressure aerosol delivery device, and (3) a percussive therapy device used for the mobilization of mucus.

2. Description of the Background Art

A fundamental aspect of providing respiratory care to a patient is the ability to provide ventilatory support to patients requiring respiratory assistance. Ventilatory support is typically provided by clinicians through the use of a manual resuscitator or an automatic ventilatory device.

Manual resuscitators are typically equipped with a self-inflating bag, a set of check valves which control the direction of inhalation and exhalation gases, and a patient interface which is usually either a face mask or a port for connection to an endotracheal tube. Manual resuscitators are usually supplied with a continuous flow of gas containing a known percentage of oxygen. The operator of a manual resuscitator inflates the patient with oxygen enriched air by squeezing the self-inflating bag thus applying pressure and causing gas to flow into the patient's lungs. Inhalation ends and exhalation begins when the operator stops squeezing the bag, allowing the pressurized gas in the patient's lungs to escape to the ambient environment. Most manual resuscitators are equipped with the means to maintain a small minimum positive pressure on the patient's lungs throughout exhalation commonly called Positive End Expiratory Pressure (PEEP). During exhalation, the self-inflating bag reinflates and the process may be repeated. Manual resuscitators are simple and inexpensive. Unfortunately, manual resuscitators are easy to misuse. A large number of studies have recently been published which show that irregardless whether the operator of the manual resuscitator is a physician, respiratory therapist or nurse, patients receive volumes of gas per breath (tidal volume) which are too small and respiratory rates which are too quick. This has been shown to create significant adverse effects on patients.

Automatic ventilatory devices (ventilators) were originally developed to deliver a set amount of volume to the patient in a set amount of time with little patient monitoring capability. In the last 25 years different modes, including pressure control, and increased monitoring capabilities have been added, leading to the modem transport ventilators of today. Most ventilators still use volume and time cycled ventilation modes which operate by delivering to the patient pre-set amount of volumes or constant flow for pre-set amounts of time, regardless of the patient's lung compliance. Lung compliance is prone to sudden changes during transport, potentially causing patient airway pressures to increase to the point that they will severely injure the patient. Pressure cycled ventilation and pressure control are newer modes of ventilation used to deliver ventilatory support to the patient and which have a number of distinct advantages over volume and time cycled ventilation modes. Pressure cycled ventilation functions by switching to exhalation from inhalation when a certain pressure is reached, regardless of the volume delivered; thus volumes of gas delivered to the patient vary with variances in lung compliances, preventing the patient from receiving a harmful amount of pressure and insuring appropriate ventilation of the patient.

Modern transport ventilators are battery or pneumatically powered and equipped with numerous ventilation modes, including pressure cycled types of ventilation, various flow control functions, multiple alarm monitoring functions and are also capable of detecting and synchronizing with the patient's breathing efforts. Although current transport ventilators provide consistent, safe and reliable ventilation, they are extremely expensive. Additionally, the disposable accessories that are required to be used with these ventilators can sometimes cost as much or more than a manual resuscitator. To reduce the high capital costs of these devices, some manufacturers have returned to offering simplified time cycled volume ventilators without any of the standard monitoring, control and alarm features of typical ventilators, nor the option of pressure cycled ventilation. These devices are often classified as automatic resuscitators and, in addition to not being as safe, still cost thousands of dollars and require the use of additional disposables or parts which require sterilization before being reused. In today's environment of medical cost containment, hospitals and other medical providers have, for the most part, balked at the cost of transport ventilators and the training of additional personnel it would require.

Therefore, a need exists for a ventilator technology which is as consistent, safe, and reliable as current transport ventilators but as inexpensive and easy to use as manual resuscitators. The present invention satisfies those needs, as well as others, and overcomes the deficiencies in prior technology.

BRIEF SUMMARY OF THE INVENTION

The present invention generally comprises a pressure pulmonary modulator apparatus which will inflate and discharge any pneumatic capacitance for a wide range of frequencies when provided with a constant flow of gas. In a first embodiment, the patient's lungs serve as the pneumatic capacitance, which is cyclically inflated and discharged (inhalation followed by exhalation), thus providing constant flow, pressure cycled ventilatory support to patients requiring respiratory assistance. Such an embodiment of the invention is as safe, effective and reliable as transport ventilators with the ease of use and associated cost of a manual resuscitator.

In a second embodiment, the pressure pulmonary modulator is in fluid communication with an attached pneumatic capacitance which may be caused to cycle at a variety of frequencies, thus providing a different type of ventilatory effect on the patient which is in constant fluid communication with the primary cavity of the pressure pulmonary modulator. The pulmonary capacitance may be configured to oscillate at frequencies up to approximately 25 Hz during the patient's exhalation, which has been shown to mobilize retained endobronchial secretions of patients suffering from congestion.

Either embodiment may be used in conjunction with a nebulizer, providing therapeutic relief, in addition to the delivered ventilatory support. In either embodiment, compressed air or oxygen is delivered directly to the pneumatic capacitor, thus charging the pneumatic capacitor. During discharge, all gas flows through the pressure pulmonary modulator. The invention cycles the pneumatic capacitor by controlling at what pressure charging ends and discharge begins and at what pressure discharge ends and charging begins. The duration of charging is controlled by the flow rate of incoming air/oxygen and is affected by the compliance of the pneumatic capacitor. The duration of discharge is controlled by a variable restrictor within the device which controls how quickly the discharged gas of the pneumatic capacitor is exhausted into the atmosphere. When the pneumatic capacitor pressure drops to a specified level, the valve of the pressure pulmonary modulator closes, and the pneumatic capacitor begins to be charged by the continuous flow of gas; thus the cycle is repeated indefinitely.

In the first embodiment, the pressure pulmonary modulator apparatus essentially comprises a dual area piston having a surface area that rests against an interior end of a primary port, thus sealing the primary port during charging of the pneumatic capacitor. The dual area piston comprises a primary area defined as the area exposed to the pneumatic capacitor during charging when the piston is in the closed position, and a much larger area which comprises the entire area of the piston which is in fluid communication with the pneumatic capacitor only during discharge or when the piston is in the open position. When the dual area piston is closed, it prevents compressed gas from escaping and causing the pneumatic capacitor to become charged by the incoming compressed gas. During charging, the pressure in the pneumatic capacitor increases until the force of the pressure on the primary area of the dual area piston overcomes the restorative force of the piston. Once the dual area piston begins to open, the full area of the piston is exposed to the pressure of the pneumatic capacitor causing the piston to move away from the interior end of the primary port to a fully open position almost immediately. When the piston fully opens, it seals against piston relief holes. The pneumatic capacitor pressure that causes the piston to move into the fully open position is the pneumatic capacitor's peak pressure, which is adjustable by controlling the restorative force on the piston. Once the piston opens, it will remain open until the pneumatic capacitor's pressure drops to a value small enough such that the force of the spring overcomes the force of the pneumatic capacitor pressure on the full area of the piston. During discharge, the exhaled gases pass by the piston and out of the system through an adjustable flow restrictor used to control the rate at which discharged gases are vented into the atmosphere, resulting in the control of discharge duration. Once the pneumatic capacitor's pressure drops to a value low enough to allow the force of the spring to push the piston closed, the discharge ends and the cycle is repeated.

In the first embodiment of the invention in which the patient serves as the pneumatic capacitor, the patient may spontaneously breathe by triggering inhalation prior to the beginning of exhalation. A one-way valve may optionally be provided to increase the ease of the patient's inhalation. Under such circumstances, a new inhalation will start when the patient breathes in, reducing the patient's airway pressure and causing the piston to close and a new inhalation period to start. In addition, the apparatus can be adapted to function as a positive pressure aerosol device by attaching a nebulizer assembly to the primary port of the apparatus. Such a device is useful to those needing the therapeutic effects of aerosol in addition to ventilatory support.

In the second embodiment where the pressure pulmonary modulator apparatus is in fluid communication with a mechanical pneumatic capacitance, the pressure pulmonary modulator apparatus can be coupled with a nebulizer to deliver both a medication aerosol and high frequency bursts of compressed gas. In such a configuration, when a patient inhales through a mouthpiece, he or she entrains air from a nebulizer, which may be equipped with an air entrainment port, and receives a large dose of aerosolized water and Albuterol Sulfate or any other medication deemed clinically appropriate. During exhalation, the patient triggers high frequency bursts of gas. If desired, the device may also be configured to deliver high frequency bursts of gas during other phases of the respiratory cycle. The delivery of aerosol and the high frequency airway oscillations are frequently called an intrapulmonary treatment, and has been shown to help mobilize patient lung secretions and fluids. It is worth noting that the second embodiment of the invention could be configured to deliver high frequency ventilation if desired. Additionally, by increasing the volume of the pneumatic capacitor and placing a fixed or variable restrictor between the pressure pulmonary modulator apparatus and the pneumatic capacitor, the second embodiment of the invention could be used to deliver volume ventilation at lower frequencies.

An object of the invention is to provide a simplified ventilator apparatus for providing constant flow, pressure cycled ventilatory support to children and adults in an emergency situation.

Another object of the invention is to provide a ventilator apparatus which is disposable and inexpensive.

Another object of the invention is to provide a ventilator apparatus which allows for the adjustment of peak pressure, positive end expiratory pressure, inspiration duration, and expiration duration.

Another object of the invention is to provide a ventilator apparatus which can allow the patient to trigger mandatory breaths or to breathe spontaneously.

Another object of the invention is to provide a ventilator apparatus which allows inhalation to be initiated by the operator of the apparatus.

Another object of the invention is to provide a ventilator apparatus which can be equipped, or have a built-in high pressure pop-off valve as a safety feature to prevent the unintended build up of patient airway pressure due to malfunction or misuse. Such a high pressure pop-off valve may be equipped with the means to produce an audible tone which will notify an operator that the patient is experiencing high airway pressures.

Another object of the invention is to provide a ventilator apparatus which can be easily used in conjunction with a nebulizer to deliver intermittent positive pressure aerosolized medication to the patient at high and low respiratory rates.

Another object of the invention is to provide a ventilator apparatus which can deliver ventilatory support to patients being transported within or in between hospitals.

Another object of the invention is to provide a ventilator apparatus which can be used to treat patients suffering from sleep apnea.

Another object of the invention is to provide a ventilator apparatus which can be used with a manual resuscitator to insure that consistent ventilatory support is being delivered to the patient.

Another object of the invention is to provide a ventilator apparatus which can provide to a patient high frequency bursts of gas.

Yet another object of the invention is to provide a ventilator apparatus which can be adapted to function as an intrapulmonary percussive therapy device.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DETAILED DESCRIPTION OF THE INVENTION

Referring more specifically to the drawings, for illustrative purposes the present invention is embodied in the apparatus generally shown in FIG. 1 through FIG. 8. It will be appreciated that the apparatus may vary as to configuration and as to details of the parts without departing from the basic concepts as disclosed herein.

Figure 1:
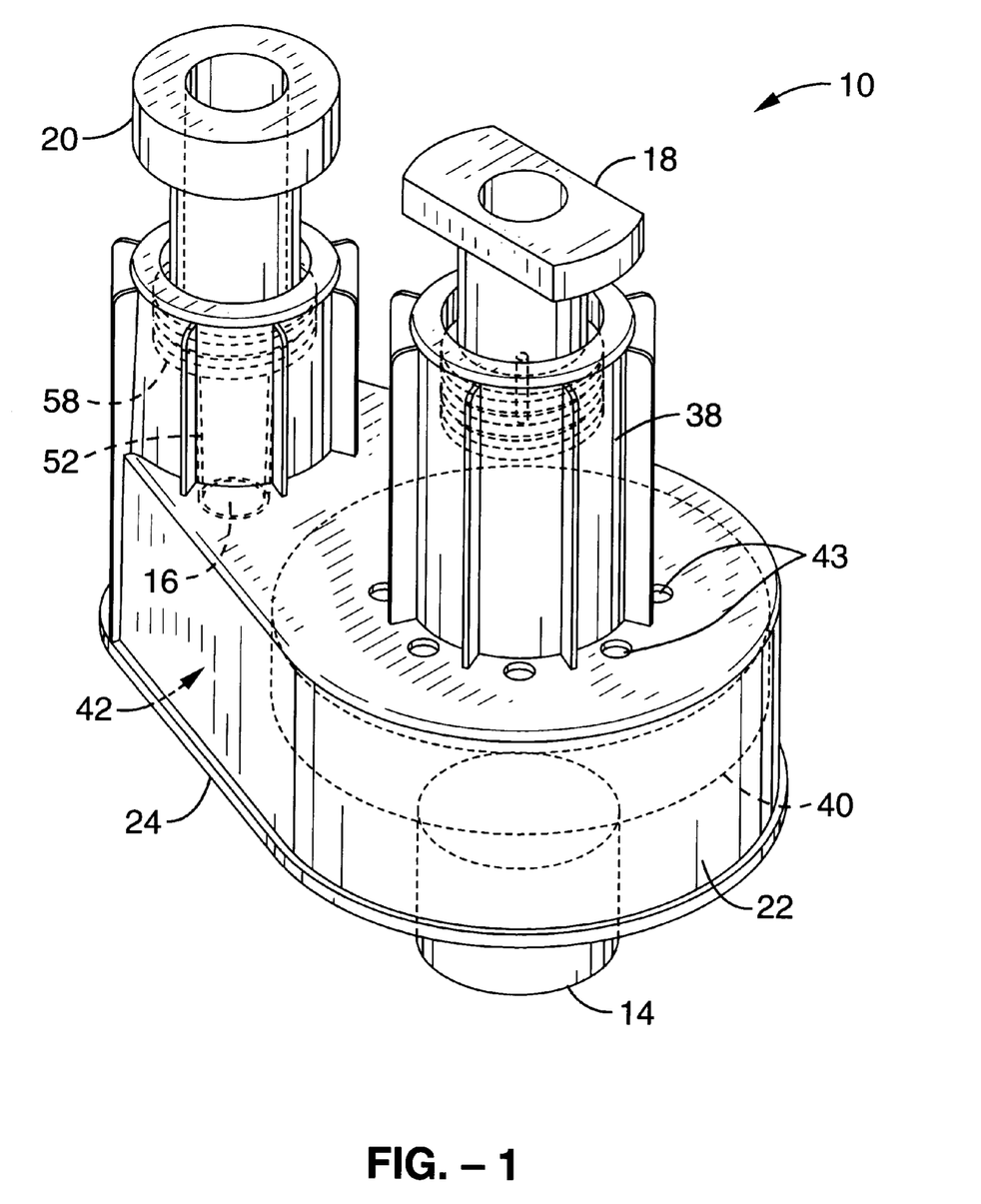
FIG. 1 is a perspective view of the pressure modulator apparatus in accordance with the present invention.
Figure 2A:
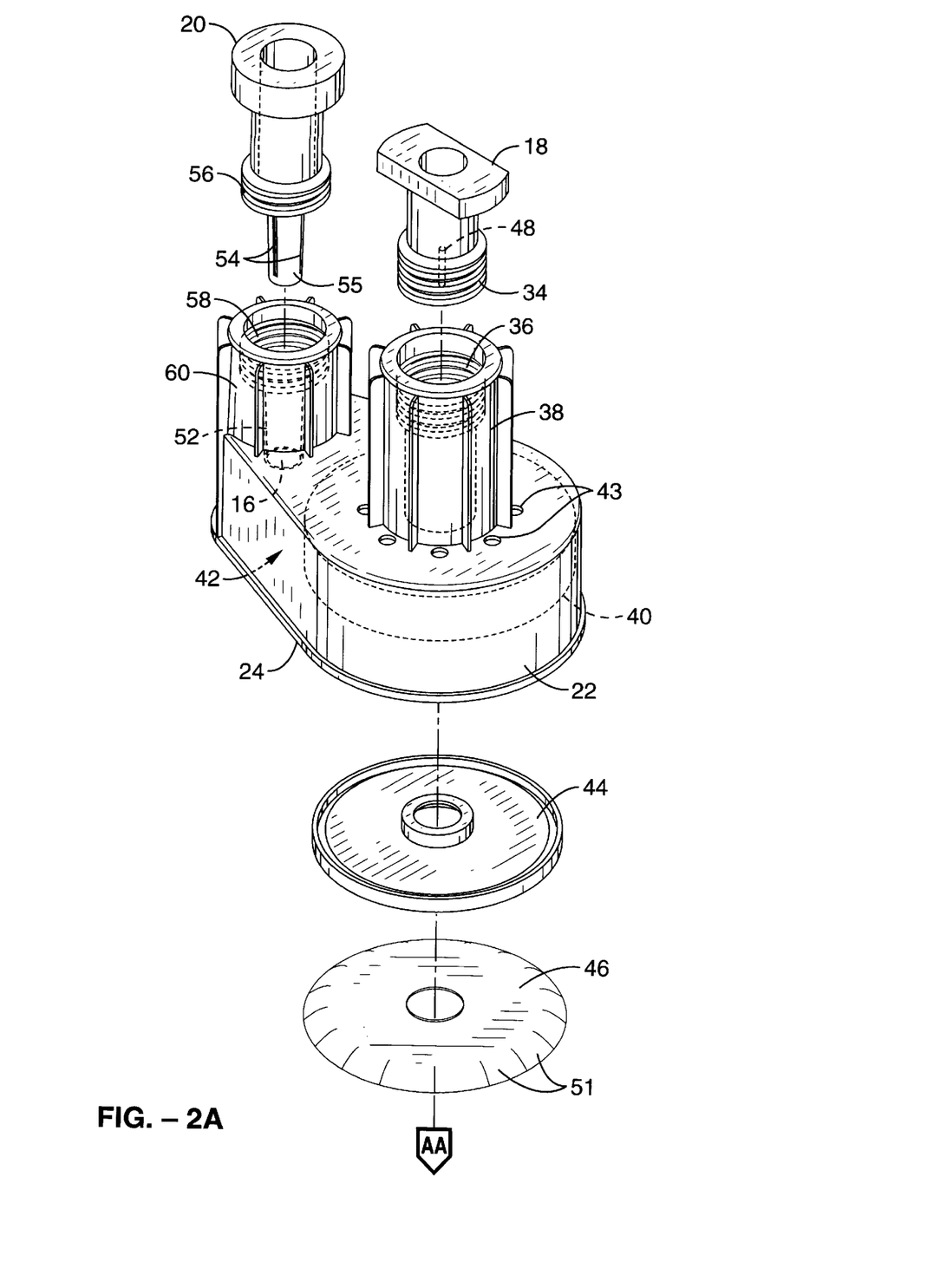
FIG. 2A and FIG. 2B are an exploded perspective view of the apparatus shown in FIG. 1.
Figure 2B:
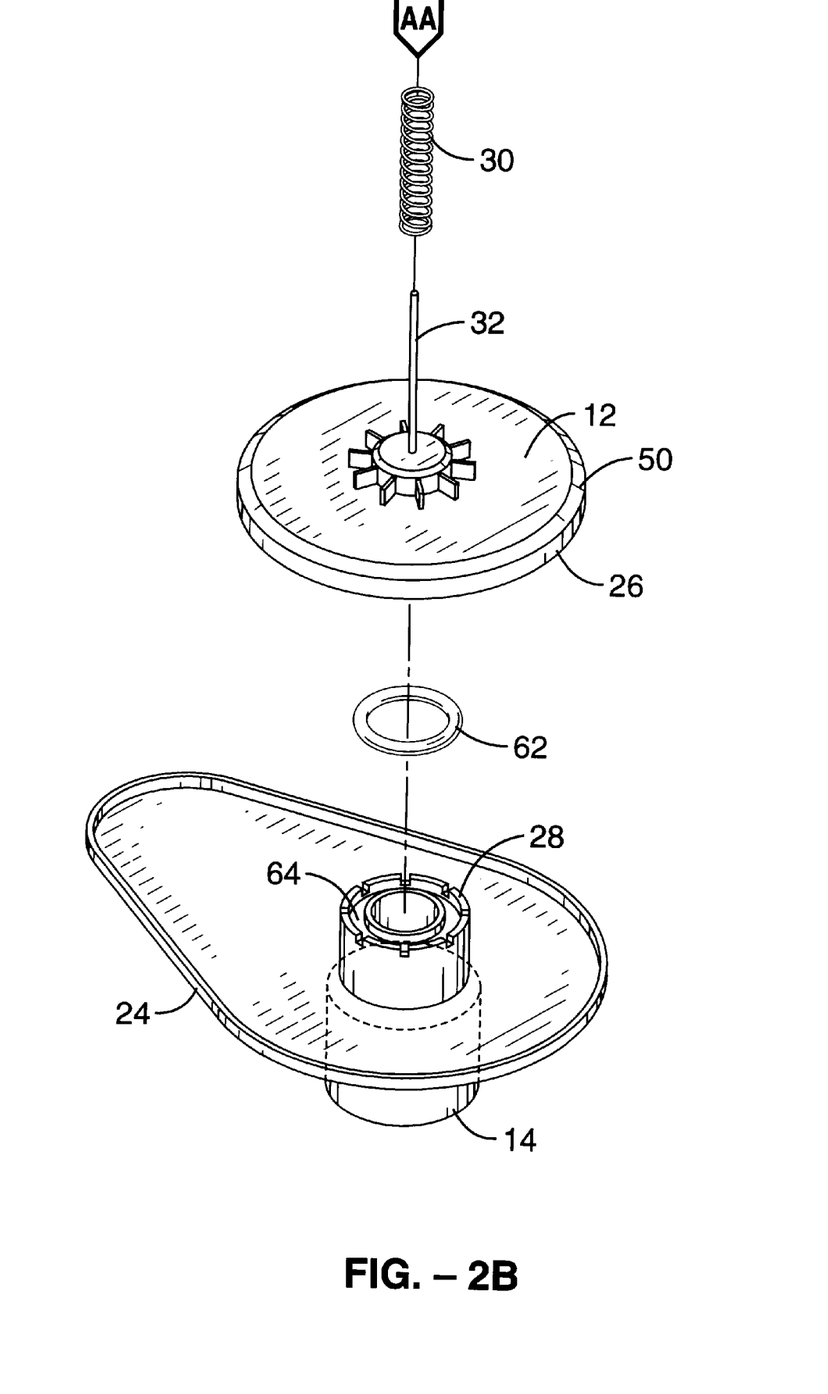

Referring first to FIG. 1, FIG. 2A and FIG. 2B a constant flow, pressure modulator apparatus 10 in accordance with the preferred embodiment of the present invention is generally shown. As will be seen, the apparatus comprises a spring-loaded piston 12, a primary port 14, a flow restrictor port 16, a pressure dial 18, a rate dial 20, a housing 22 and a base 24. The apparatus of the preferred embodiment is fabricated almost completely of injection molded plastic.

Piston 12 is normally biased in a closed position wherein the piston face 26 rests against the interior end 28 of primary port 14. A spring 30 is located around a piston stem 32 which maintains spring 30 in a substantially perpendicular orientation relative to piston face 26. External threads 34 on pressure-dial 18 engage internal threads 36 within the pressure dial boss 38, which is located atop housing 22. Rotating pressure dial 18 causes pressure dial 18 to move longitudinally relative to piston face 26, thereby increasing the compressive force on spring 30 as pressure dial 18 is moved closer to piston face 26. Pressure dial 18 therefore allows adjustment of the compressive force of spring 30 against piston 12. Piston face 26 moves longitudinally within a cylindrical sleeve 40 located within housing 22 and is in flow connection with a chamber 42 within housing 22. Piston relief holes 43 at the top of cylindrical sleeve 40 prevent entrapped air from retarding the upward motion of piston 12 within cylindrical sleeve 40 as the piston moves to the fully open position.

A ring 44, and a seal 46 which is preferably made of a polyethylene or like material, snap on to piston 12 and serve to seal piston 12 within cylindrical sleeve 40. When piston 12 is in the fully open position, piston face 26 is spaced apart from interior end 28 of primary port 14. Seal 46 extends beyond the diameter of piston 12 and ring 44 holds seal 46 in place onto piston 12. Seal 46 prevents gases from passing around piston face 26 and exiting chamber 42. Piston stem 32 travels in axial channel 48 located within pressure dial 18. The piston has a 45° chamfer 50 around its circumference which orients the flaps 51 of seal 46 so that flaps 51 overlap around the circumference of piston 12, providing some self-sealing when pressurized. Use of ring 44 and seal 46 around piston face 26 allows for looser tolerances between the outer diameter of piston 12 and the inner diameter of cylindrical sleeve 40, thus making the device easier to manufacture, more consistent and reliable. Although the preferred embodiment discloses a spring-loaded piston 12 to provide a restoring force to seal interior end 28 of primary port 14, it should be apparent to those skilled in the art that other means could be employed for this purpose, examples of which may include, but are not limited to the following: a compressed air spring; a sealed diaphragm; a balloon; an expandable chamber; a rigid chamber with compressed air and bellows.

Flow restrictor port 16 is located within housing 22 and is in flow connection with chamber 42. Rate dial 20 allows for adjustment of the rate of gas escaping from chamber 42 to the atmosphere, and adjusting rate dial 20 allows control of a patient's exhalation duration. An annular flow restrictor valve seat 52 is located within flow restrictor port 16. Flow restrictor valve seat 52 functions in conjunction with tapered inner end 55 of rate dial 20 to restrict gas from passing through flow restrictor port 16. Slots 54 in rate dial 20 have a much larger cross-sectional area than flow restrictor port 16 at its largest setting and poses little restriction to flow. The restricting area between flow restrictor valve seat 52 and the tapered inner end 55 of rate dial 20 is adjustable by positioning rate dial 20 axially through use of external threads 56 on rate dial 20 which engage internal threads 58 within the rate dial boss 60, whereby rotating rate dial 20 causes tapered inner end 55 to move longitudinally relative to flow restrictor valve seat 52. Flow restrictor valve seat 52 and tapered inner end 55 at the inner end of rate dial 20 functions similar to a needle valve to create a restrictive annular region to restrict the flow of gas therethrough. Slots 54 remain of constant cross-sectional area throughout the adjustment range of rate dial 20. Use of tapered inner end 55 and annular valve seat 52 provides for a sensitive adjustment of gas flow resistance. Although the preferred embodiment discloses using a tapered inner end 55 of rate dial 20 with slots 54 therein along with flow restrictor valve seat 52 to restrict gas flow therethrough, those skilled in the art would recognize that other means for providing adjustable gas flow resistance exist.

During the pneumatic capacitor charging period, piston face 26 rests against interior end 28 of primary port 14. This constitutes piston 12 being in a closed position. An O-ring 62 located within a groove 64 circumscribing interior end 28 of primary port 14 provides an airtight seal when piston face 26 rests against interior end 28 of primary port 14. While piston face 26 is resting against interior end 28 of primary port 14, the force of the pneumatic capacitor pressure on piston face 26 is equal to the product of the pneumatic capacitor's airway pressure and the area circumscribed by O-ring 62. As the pneumatic capacitor inflates, the pneumatic capacitor's pressure will increase until the force of the patient's airway pressure on piston face 26 overcomes the compressive force of spring 30, which causes piston 12 to open (when piston face 26 moves away from interior end 28 of primary port 14). Once piston 12 begins to open, compressed gas from the pneumatic capacitor enters chamber 42 and rushes toward flow restrictor port 16 where the passage of gas through flow restrictor port 16 is restricted by annular flow restrictor valve seat 52 and tapered inner end 55 of rate dial 20. This gas restriction causes the pressure in the chamber to quickly rise to the pressure of the pneumatic capacitor, thus applying force to the entire area of the piston face 26 and causing piston 12 to move up to a filly open position (when piston 12 is at the top of cylindrical sleeve 40). When piston 12 fully opens, it causes ring 44 to seal against piston relief holes 43.

The pneumatic capacitor pressure that causes piston 12 to move into the fully open position is the pneumatic capacitor's peak pressure and is immediately followed by discharge of the pneumatic capacitor. Once piston 12 opens, it remains open until the pneumatic capacitor pressure drops to a value low enough such that the restorative force of spring 30 on piston 12 overcomes the force of the pneumatic capacitor pressure, which is the product of the pneumatic capacitor pressure and the full frontal area of piston face 26. At this point, the piston 12 closes and discharge ends. The cycle is then repeated. Note that discharge time is adjustable by varying gas restriction. The pneumatic capacitor pressure when piston 12 closes is the pneumatic capacitor's baseline discharge pressure. When applied in the configuration where the patient serves as the pneumatic capacitor, the pressure when the piston 12 closes corresponds to the positive end expiratory pressure (PEEP).

Although not necessary or optimum for function, it is recognized that a means for preventing gas from flowing during discharge may be accomplished by using the stem of the piston as an actuator or such means as adding some other pressure sensing and actuating means to stop incoming gas from flowing during discharge, which is not used by the pneumatic capacitor. Although such a feature would decrease the amount of gas required to operate the apparatus, it would increase the complexity of the apparatus.

Figure 3:
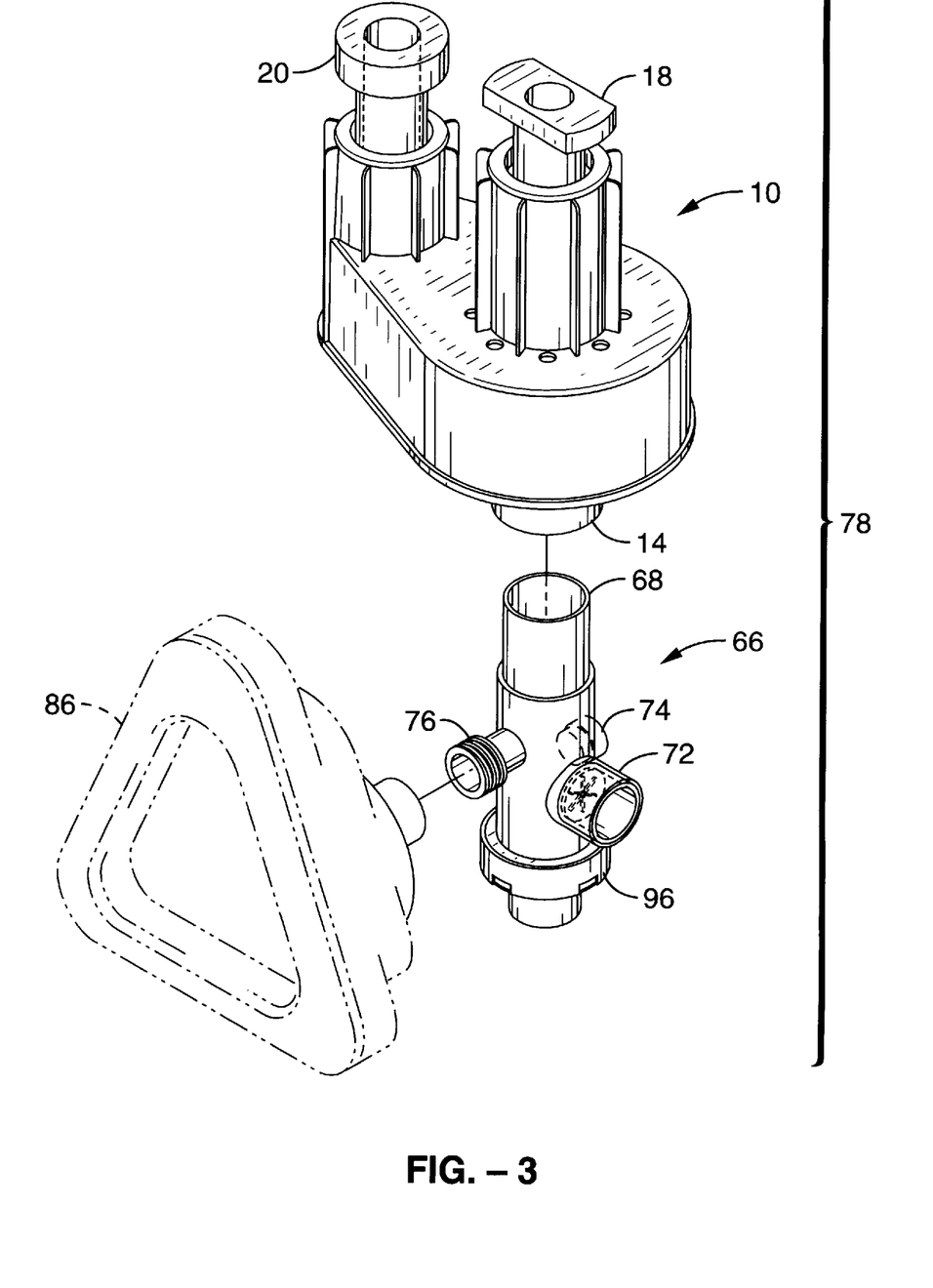
FIG. 3 is an exploded perspective view of the apparatus shown in FIG. 1 and a patient tee adapter in accordance with the invention adapted to function as a resuscitation device with a face mask shown in phantom.
Figure 4:
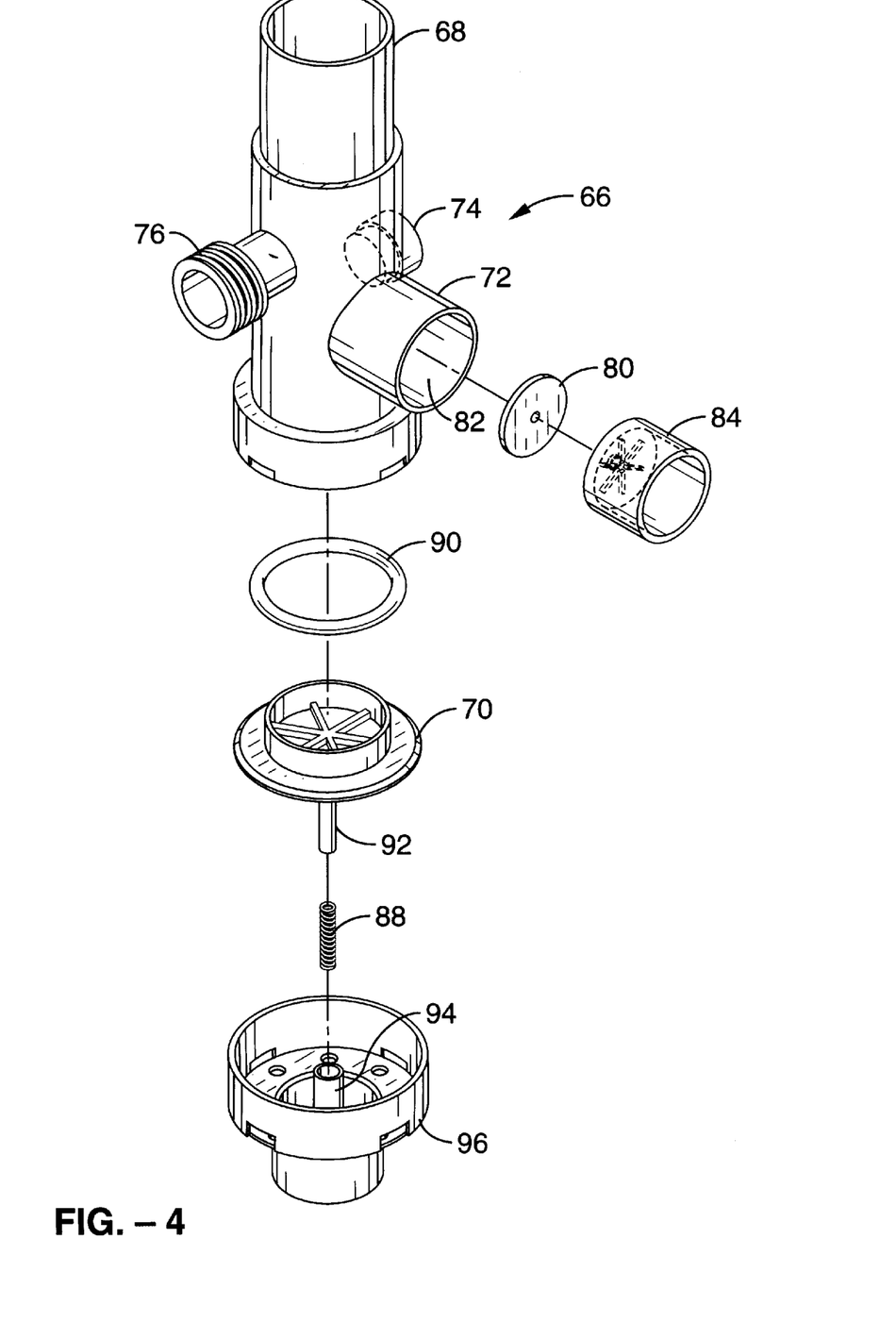
FIG. 4 is an exploded perspective view of the patient tee adapter shown in FIG. 3.

Referring also to FIG. 3 and FIG. 4, pressure modulator apparatus 10 and a patient adapter 66 are shown combined together to function as an automatic resuscitator or ventilator 78. Here, the patient effectively acts as the pneumatic capacitor. Patient adapter 66 is attached to primary port 14 of pressure pulmonary modulator apparatus 10 via attachment port 68. Patient adapter 66 is equipped with a pop-off valve 70, a patient demand valve 72, a gas inlet port 74 and a patient connection port 76. The combination of pressure modulator apparatus 10 and patient adapter 66 serves as a resuscitator 78.

Gas inlet port 74 allows connection to a source of compressed gas (not shown), such as compressed air or oxygen. The compressed gas source is attached to gas inlet port 74 using a DISS connector (not shown). Internal to gas inlet 74 is an orifice sized to ensure that for an approximate 50 psig compressed gas source, the flow will not exceed approximately 40 liters/minute. Typically, the compressed gas would consist entirely of 100% compressed oxygen but a clinician may use any type of compressed gas as deemed appropriate. The compressed air or oxygen is delivered directly to the patient for inhalation.

Patient demand valve 72 is a one-way valve, comprising of a flapper 80 placed between a one-way valve port 82 and a valve body 84, which allows air to be entrained from the room environment. Patient demand valve 72 allows the patient to draw in more air than that which is being continuously supplied to patient adapter 66 through gas inlet port 74 from the compressed gas source, thus giving the patient not only the means to initiate the beginning of inhalation but also the duration. In the preferred embodiment, patient demand valve 72 has a very low resistance to flow, which is on the order of approximately 3.5 cm $H_2O$@50 liters/minute.

Patient connection port 76 allows a connection of a breathing mask 86 or an endotracheal tube (not shown) which the patient wears during the breathing process associated with resuscitator 78. Because the piston 12 is closed during inhalation, all incoming gas is delivered to the patient through patient connection port 76. In the preferred embodiment, patient connection port 76 has a 22 mm OD for connection to PEEP masks (not shown) and a 15 mm ID for connection to endotracheal tubes.

Pop-off valve 70 provides a safety feature to prevent the patient airway pressure from exceeding any set value. Pop-off valve 70 is biased by spring 88 and equipped with a sealing O-ring 90. Pop-off valve 70 opens anytime the patient's airway pressure exceeds a preset value. Pop-off valve 70 has a stem 92 which travels within an axial tube 94 within end cap 96. Pop-off valve 70 can also be equipped with a means to create an audible tone and a visual signal when the valve 70 is opened.

When inhalation pressure reaches that which is dialed on pressure dial 18, piston 12 moves to the fully open position, as discussed above. In the preferred embodiment, the ratio of the pneumatic capacitor's peak pressure to the pneumatic capacitor's baseline pressure is 10:1, which is consistent with the ratio of the full surface area of piston face 26 and the surface area circumscribed by O-ring 62. Pressure dial 18 and pulmonary modulator spring 30 are designed so that the resuscitator delivers a maximum pneumatic capacitor peak pressure of approximately 55 cm $H_2O$ and a minimum pneumatic capacitor peak pressure of approximately 20 cm $H_2O$, although this is not the physical limit of the apparatus. Pop-off valve 70 is designed to relieve pressure if the patient's airway pressure rises above approximately 60 cm $H_2O$.

It will be appreciated that patient adapter 66 may also include a dump valve which is in fluid connection with the patient's airway, thus allowing for the quick discharge of exhaled gas when opened and, when re-closed, allowing for quick restart of inhalation.

Figure 5:
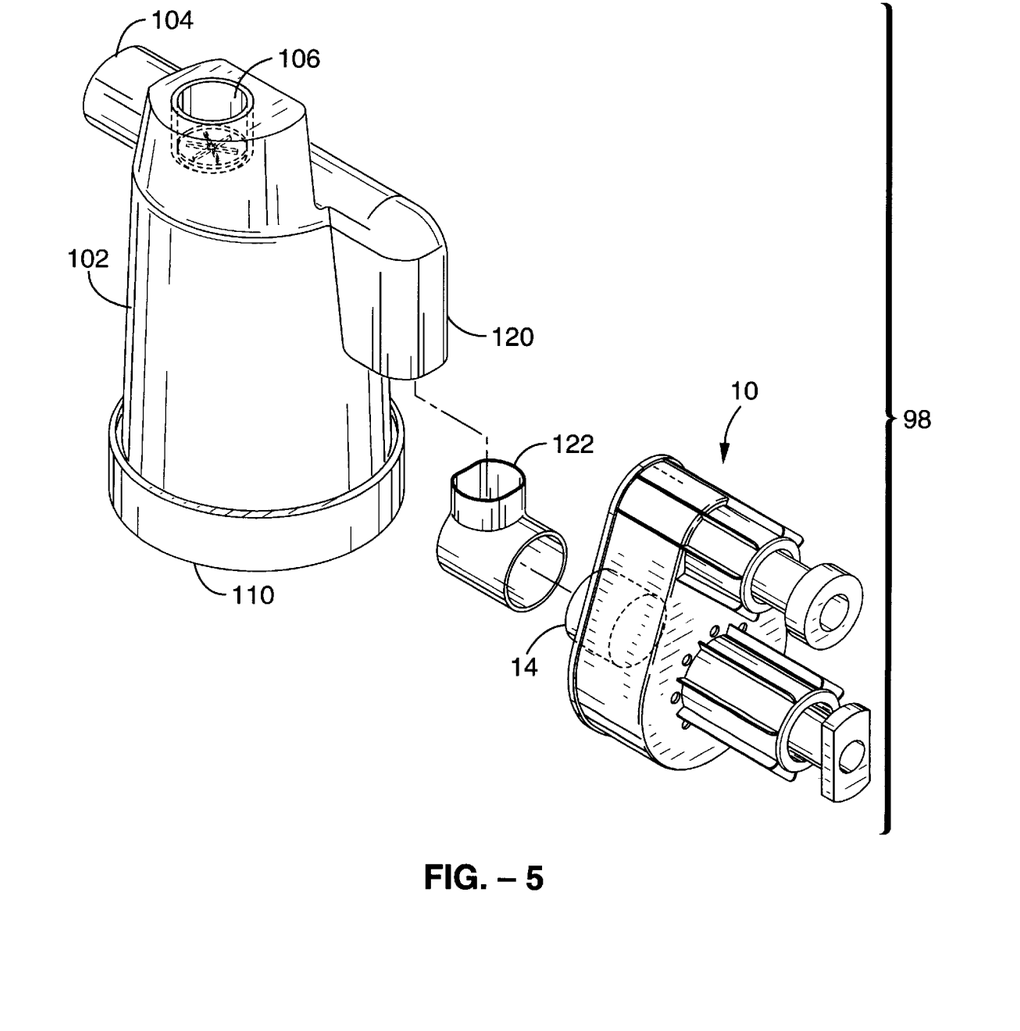
FIG. 5 is an exploded perspective view of the apparatus shown in FIG. 1 and a nebulizer in accordance with the invention adapted to function as a positive pressure aerosol device.
Figure 6A:
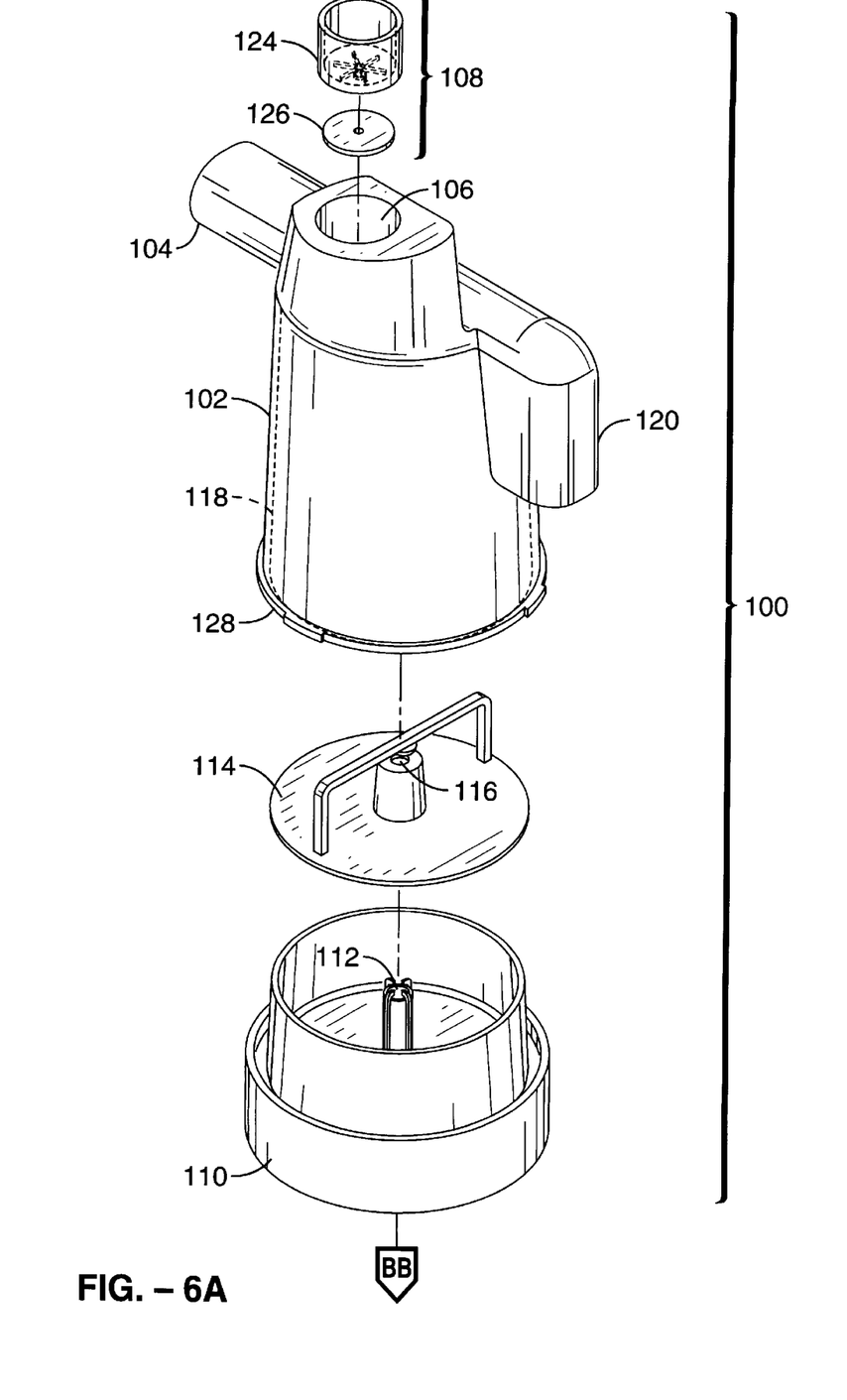
FIG. 6A and FIG. 6B are an exploded perspective view of a percussive therapy device in accordance with the invention using the nebulizer shown in FIG. 5.

Referring also to FIG. 5 and FIG. 6A, pulmonary modulator apparatus 10 can be adapted to function as a positive pressure aerosol device 98, wherein a nebulizer assembly 100 is attached to primary port 14 of pulmonary modulator apparatus 10. Such a device functions identically as previously described with a nebulizer assembly 100 replacing patient adapter 66, and is useful for providing to people the therapeutic effect of aerosol in conjunction ventilatory support or treatment. Nebulizer assembly 100 generally comprises a top cover 102 having a mouthpiece 104, an air entrainment port 106, a one-way air demand valve assembly 108, a reservoir 110 with a primary orifice 112 located therein, and a baffle 114 with a secondary orifice 116. In this configuration, there is no pop-off valve and the patient breathes through mouthpiece 104.

Top cover 102 includes a nebulizer chamber 118 located beneath, one-way demand valve 108 built into the upper portion of the top cover 102, and an elbow receptacle 120 which allows nebulizer assembly 100 to be attached to primary port 14 of the pulmonary modulator apparatus 10 via an elbow connector 122. One-way demand valve assembly 108 permits air to be entrained into positive pressure aerosol device 98 as may be desired during use by the patient but does not allow any gas pressure to escape externally. Demand valve assembly 108 includes a cylindrical valve body 124 inserted into an air entrainment port 106 located adjacent the upper portion of top cover 102. A flapper 126 is inserted into air entrainment port 106 between top cover 102 and valve body 124. Demand valve assembly 108, elbow receptacle 120 and mouthpiece 104 are in fluid communication with nebulizer chamber 118 and reservoir 110.

Reservoir 110 is attached to base 128 of top cover 102 by an airtight sealing means, such as a glue sealant or the like. Baffle 114 and secondary orifice 116 are located between nebulizer chamber 118 and reservoir 110. The primary 112 and secondary 116 orifices are in fluid communication with nebulizer chamber 118 and are located in series with each other, with secondary orifice 116 being above primary orifice 112. Reservoir 110 stores the fluid to be aerosolized when the patient inhales through mouthpiece 104, and in this configuration, also includes a barb (not shown) on the underside of reservoir 110. The barb allows for connection of nippled oxygen tubing which is commonly used in hospitals to supply compressed gas. Those skilled in the art will appreciate that many different nebulizers and pneumatic arrangements may be used to perform the same function.

Figure 6B:
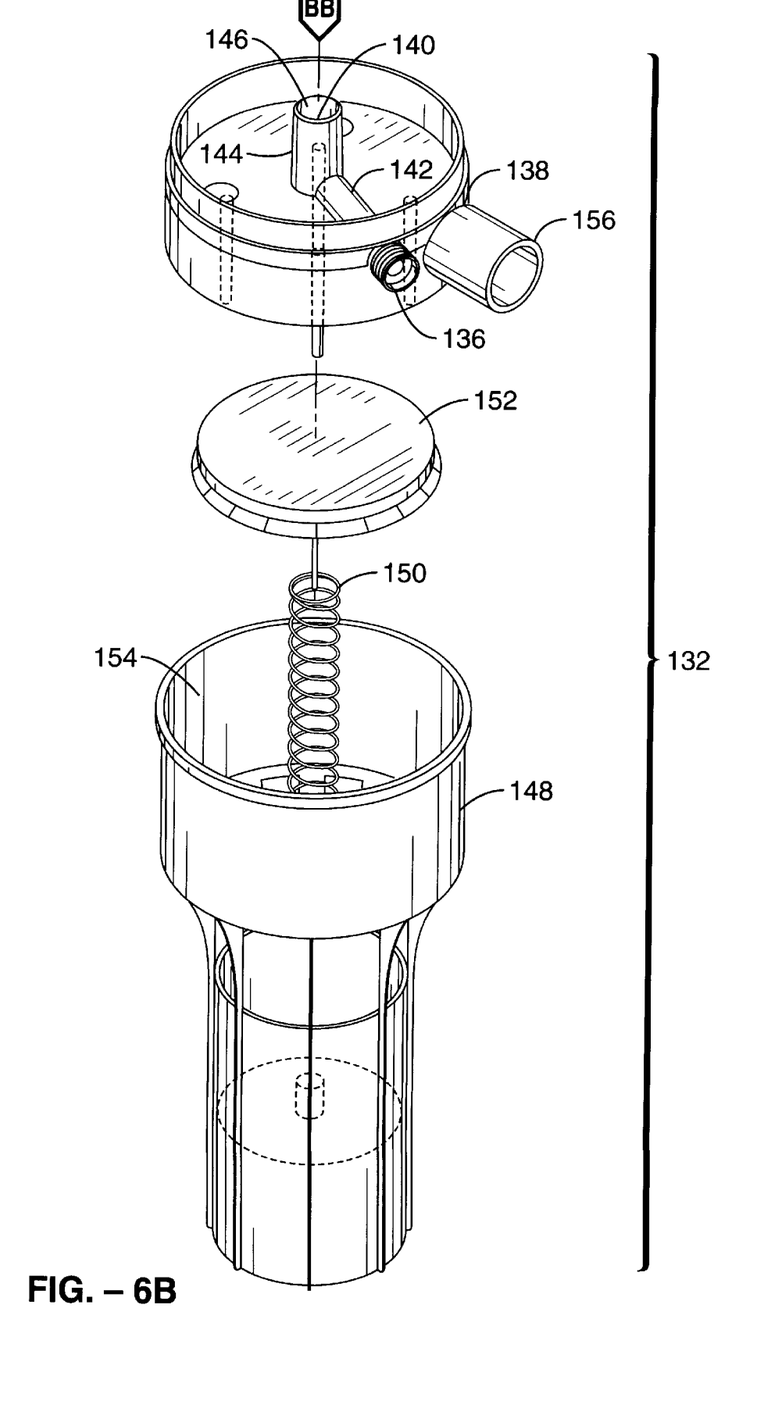
Figure 7:
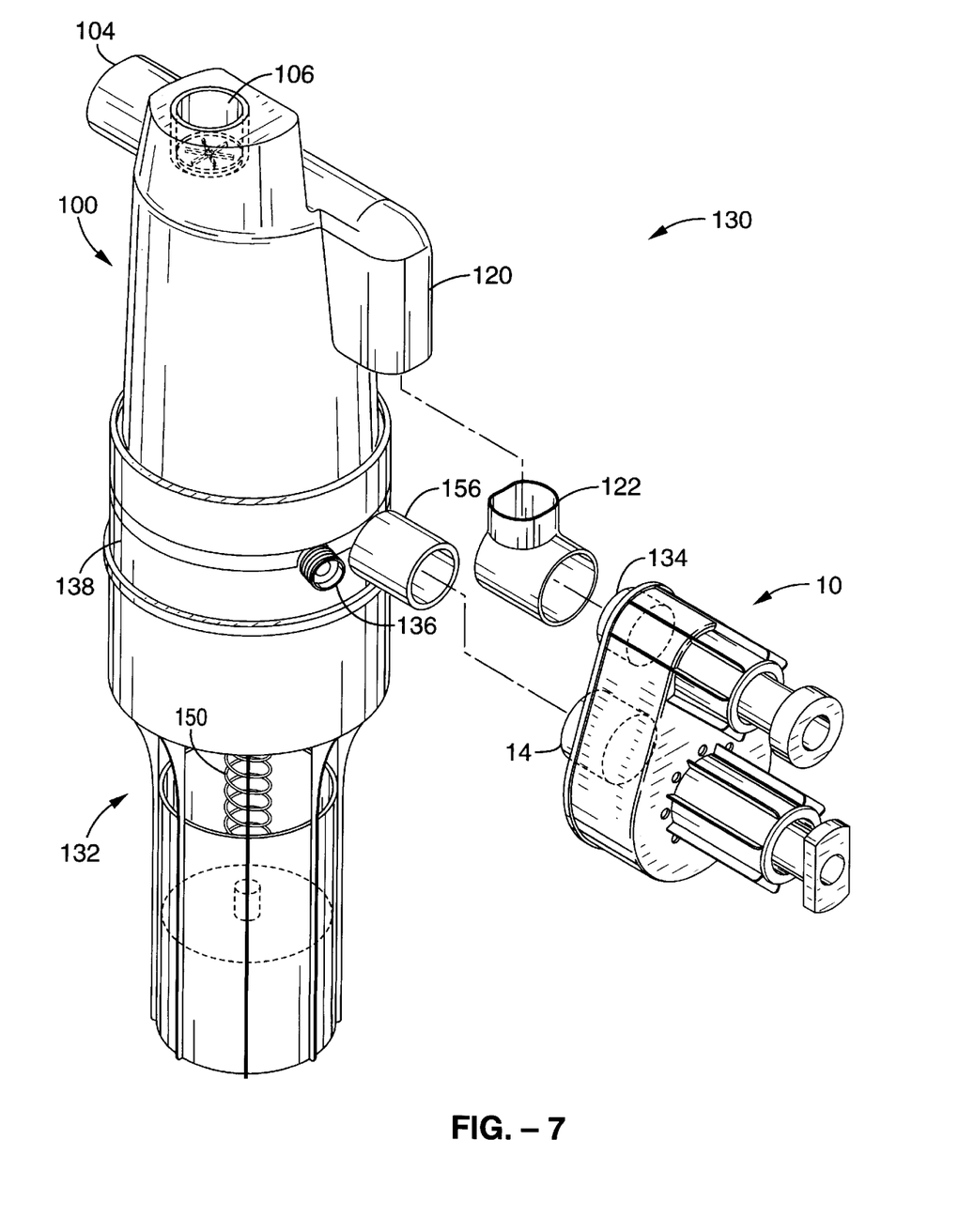
FIG. 7 is an exploded perspective view of an assembly for percussive therapy using a two port embodiment of the apparatus shown in FIG. 1 coupled to the percussive therapy device shown in FIG. 6A and FIG. 6B.
Figure 8:
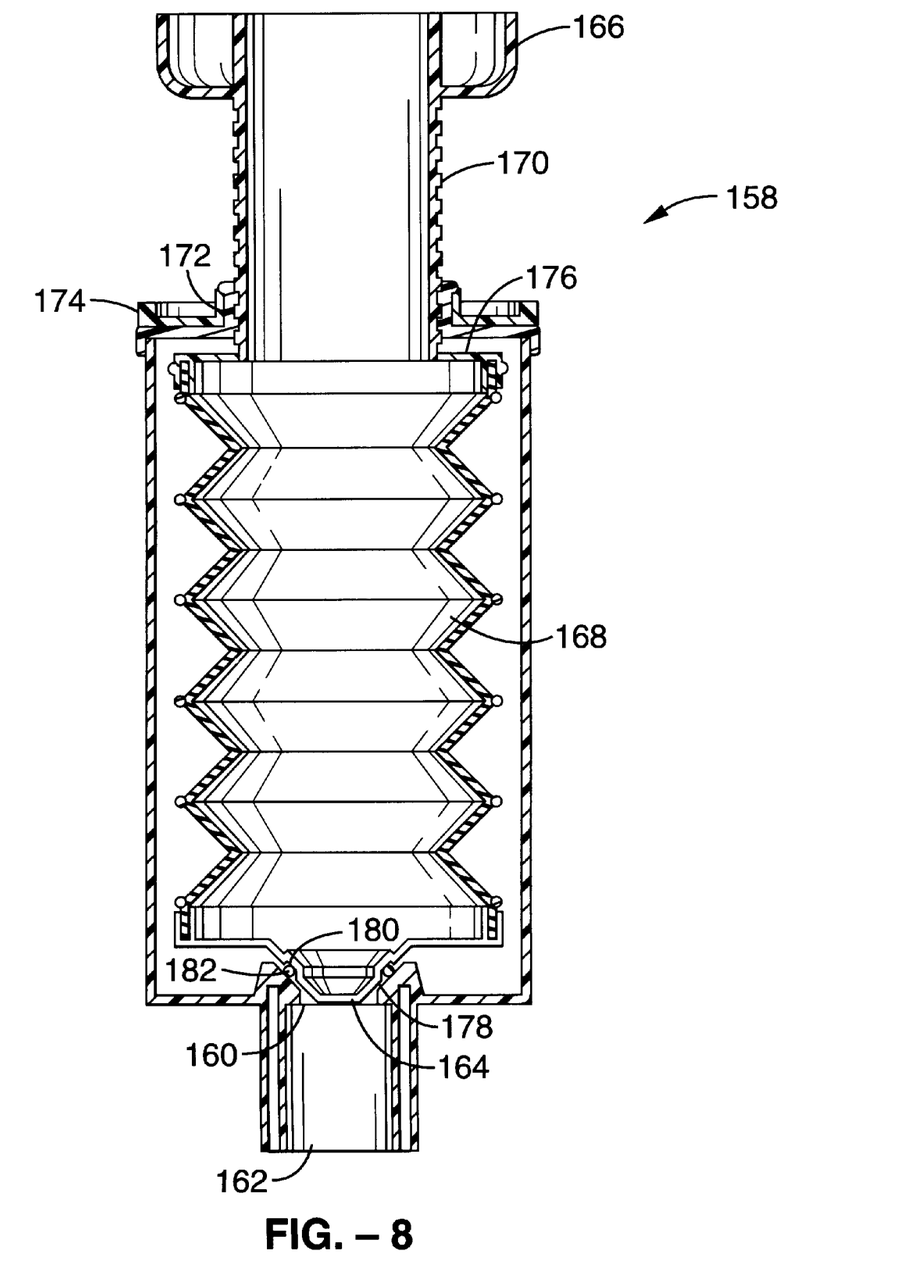
FIG. 8 is a side elevation view of a diaphragm as an alternative embodiment to the piston shown in FIG. 2A and FIG. 2B.

Referring also to FIG. 6B and FIG. 7, pressure modulator apparatus 10 can be adapted to function as a percussive therapy device (PTD) 130. Here, pressure modulator apparatus 10 is attached to outlet 156 of pneumatic capacitor assembly 132 via primary port 14 on pressure modulator apparatus 10. Elbow receptacle 120 of nebulizer assembly 100 is connected to pressure modulator apparatus 10 using elbow connector 122 attached to a secondary port 134 on pressure modulator apparatus 10 for this configuration.

Percussive therapy device 130 delivers both a medication aerosol and high frequency bursts of compressed gas. When a patient inhales through mouthpiece 104, the patient entrains air through air entrainment port 106 and receives a large dose of aerosolized water and Albuterol Sulfate (or any other medication deemed clinically appropriate). During exhalation, the patient triggers high frequency bursts of air that oscillate at frequency up to approximately 25 Hz and at a peak pressure up to approximately 120 cm H$_2$O. The delivery of aerosol and the high frequency airway oscillations help mobilize patient lung secretions and fluids.

PTD 130 functions by receiving compressed gas, typically above approximately 15 psig, through compressed gas inlet 136. Compressed gas inlet 136 is built into pneumatic capacitor top 138 and supplies compressed gas through a channel 142 within pneumatic capacitor top 138 to pneumatic capacitor assembly 132 as well as to primary orifice 112 within nebulizer reservoir 110. A choke 140 is located within a choke tube 144. The fluid communication of choke 140 and primary orifice 112 is accomplished by having a gas inlet (not shown) beneath nebulizer reservoir 110 that is pressed and glued into choke tube 144 of pneumatic capacitor top 138 which is equipped with a port 146. In the preferred embodiment of PTD 130, choke 140 preferably has three times the cross sectional area of primary orifice 112. This ensures that approximately 75% of the incoming gas flow goes to pneumatic capacitor assembly 132 and approximately 25% goes to nebulizer assembly 100. Pneumatic capacitor assembly 132 is a pneumatic energy storage device in which a given amount of pressure will create a volume displacement, thus storing fluid energy.

Pneumatic capacitor assembly 132 comprises a pneumatic capacitor top 138, a pneumatic capacitor bottom 148, a pneumatic capacitor spring 150, and a pneumatic capacitor piston 152. Pneumatic capacitor piston 152 is located within pneumatic capacitor bottom 148 and forms a variable displacement chamber 154 when pneumatic capacitor top 138 is attached onto pneumatic capacitor bottom 148. In the preferred embodiment, pneumatic capacitor piston 152 is of identical design as pressure modulator piston 12. The volume above pneumatic capacitor piston 152 and below pneumatic capacitor top 138 represent the volume in which the pneumatic energy is stored. As the pressure in this volume is increased, a volume displacement occurs through the pressure acting on the top of pneumatic capacitor piston 152 which in turn, pushes against pneumatic capacitor spring 150. Piston 152 has a maximum length of free travel which places a maximum limit on the displaced volume of approximately 75 ml. The pneumatic volume is in fluid communication with pneumatic capacitor choke 140 and pneumatic capacitor outlet 156, which in turn is in fluid communication with primary port 14 of pressure modulator apparatus 10.

The pressure modulator apparatus 10 used with PTD 130 is of identical design as that used with resuscitator 78 and positive pressure aerosol device 98, except for two minor variations: (1) pressure spring 30 typically has a much higher spring rate and consequently opens at higher pressures, and (2) pressure modulator apparatus 10 is equipped with a secondary connection port 134. It should be noted that any number of different springs can be used to accomplish different pulmonary effects. When pressure modulator piston 12 is closed, pneumatic capacitor choke 141 is delivering gas to the pneumatic capacitor causing the pressure to rise and volume to be displaced. When the pressure inside PTD 130 becomes high enough, the forces on pressure modulator piston 12 will be high enough to overcome the restoring force of pressure modulator spring 30, at which point pressure modulator piston 12 moves to the fully open position and remains there until the pressure in modulator chamber 42 drops to a value low enough that it is overcome by the restoring force of spring 30. Gas escapes through modulator primary port 14 which has a restriction such that pneumatic capacitor assembly 132 is allowed time to empty almost its entire volume quickly. During exhalation, this cycling of pneumatic capacitor piston 152 and pressure modulator piston 12 occurs at a frequency up to approximately 25 Hz depending on the rate of incoming flow to pneumatic capacitor assembly 132, the restoring force of pressure spring 30, and the setting of rate dial 20 which controls the resistance to exiting flow and the exhalation flow of the patient. These settings also control the peak pressure experienced by the patient each cycle. In the preferred embodiment of PTD 130, the restoring force of pressure spring 30 and rate dial 20 will be kept constant and the patient or clinician will adjust the frequency and amplitude by simply adjusting the incoming flow. The total flow ranges between approximately 35 L/min to 60 L/min with peak pressure up to approximately 120 cm of $H_2O$ and frequency up to approximately 25 Hz, respectively. Approximately 25% of the total flow is continuously going to the nebulizer assembly 100.

During inhalation, the patient entrains air through nebulizer air entrainment port 106, which channels the incoming air through the nebulizer assembly 98, dramatically increasing the aerosol inhaled by the patient. Typically, the modulator will not cycle during inhalation because the pressure of the patient's inhalation on the full area of the piston combined with the restoring force is greater than the pneumatic capacity pressure force. It is a distinct advantage of PTD 130 that it cycles primarily during exhalation because it insures that during the time the mucus is being mobilized, the average speed of gas in the lungs is directed out and not into the lung. In the event that cycling during other phases of the respiratory cycle were beneficial, PTD 130 could be configured in that manner as well. It is also important to note that PTD 130 is a high frequency ventilator of sorts and that a type of volume ventilator may be created by simply taking the currently described PTD 130 and drastically increasing the volume of the pneumatic capacitor. Although such a device would be significantly bulkier, and would not necessarily need the nebulizer, it is not known how well such a modification would function with spontaneously breathing patients.

FIG. 8 illustrates a sealed diaphragm and valve assembly 156 as alternative means to provide a seal to interior end 160 of primary port 162 and the restorative force required for the valve to overcome the pneumatic capacitor's pressure during exhalation, thus sealing interior end 160 of primary port 162. A dial 166 is located atop the sealed diaphragm 168. Dial 166 has external threads 170 which threadably engage internal threads 172 on the housing 174 such that rotating dial 166 causes it to move longitudinally relative to housing 174. Dial 166 is engaged within housing 174 to the extent that it abuts the top 176 of sealed diaphragm 168, whereby rotating the dial 166 in one direction causes it to compress diaphragm 168 and rotating it in another direction causes it to decompress diaphragm 168. Thus, dial 166 allows adjustment of sealed diaphragm's 168 internal pressure. Although this configuration illustrates interior end 160 of primary port 162 having a tapered seat 178 which mates with valve 164 to seal the interior end 160 of primary port 162, any similar means of sealing interior end 160 of inlet port 162 will suffice. Valve 164 is circumscribed by a groove 180 within which an O-ring 182 is fitted. When diaphragm 168 is in the closed position as shown, O-ring 182 rests against the tapered seat 178.

Although the description above contains many specificities, these should not be construed as limiting the scope of the invention but as merely providing illustrations of some of the presently preferred embodiments of this invention. Thus the scope of this invention should be determined by the appended claims and their legal equivalents.

What is claimed is:

1. An apparatus for modulating airway pressure of a patient, comprising:

(a) a chamber;

(b) a port having an interior end and an exterior end, said interior end in flow communication with said chamber;

(c) a valve, said valve including a first actuation area in flow communication with said port when said interior end is closed by said valve, said valve including a second actuation area in flow communication with said port when said interior end is open, said first actuation area being less than said second actuation area, wherein said valve is configured to open and close by changes in flow pressure applied to said port, and wherein the pressure required to open said valve is greater than the pressure required to hold said valve open; and (d) a biasing member that provides a restorative biasing force on said valve, wherein said valve is normally biased in a position wherein said port is closed, and wherein said pressure applied to said port opposes said restorative biasing force.

2. An apparatus as recited in claim 1, further comprising a flow restrictor on said chamber and in flow communication with said port when said interior end of said port is open.

3. An apparatus as recited in claim 2, wherein said flow restrictor comprises:

(a) a flow restrictor port; and (b) a dial, said dial including an inner end and an outer end, said inner end engaged within said flow restrictor port and capable of axial movement within said flow restrictor port, said inner end in fluid connection with said outer end.

4. An apparatus as recited in claim 1, further comprising means to adjust the restorative force provided by said biasing member on said valve.

5. An apparatus as recited in claim 1, wherein said valve comprises:

(a) a piston assembly, said piston assembly including a piston with a piston face, said piston face positioned adjacent said interior end so as to seal said interior end; and (b) a sleeve, said sleeve located within said chamber, wherein said piston assembly is engaged within said sleeve, and wherein said piston is capable of reciprocating axial movement within said sleeve.

6. An apparatus as recited in claim 5, wherein said piston assembly comprises:

(a) a spring, said spring biasing said piston face adjacent said interior end; and (b) a piston seal, wherein said seal is positioned circumferentially about said piston face.

7. An apparatus as recited in claim 1, further comprising:

(a) an adapter body;

(b) a connection port in fluid communication with said adapter body, said connection port attached to said exterior end of said port;

(c) a gas inlet port in fluid communication with said adapter body whereby a compressed gas source can be attached to said adapter body; and (d) a patient connection port in fluid communication with said adapter body.

8. An apparatus as recited in claim 7, further comprising:

(a) a one-way flapper valve, said flapper valve in fluid communication with said adapter body, said flapper valve capable of permitting airflow into said adapter body; and (b) means to automatically release gas pressure from within said adapter body.

9. An apparatus as recited in claim 1, further comprising a nebulizer connected to said port.

10. An apparatus as recited in claim 9, wherein said nebulizer comprises:

(a) a nebulizer cap, said cap further comprising a nebulizer chamber, a mouthpiece and an elbow receptacle, said mouthpiece and said elbow receptacle in fluid communication with said nebulizer chamber, said elbow receptacle in fluid communication with said chamber of said apparatus;

(b) a reservoir sealably attached to said cap, said reservoir including a primary orifice, said primary orifice in fluid communication with said nebulizer chamber; and (c) a baffle, said baffle located within said reservoir, said baffle including a secondary orifice, said secondary orifice in fluid communication with said nebulizer chamber. and (b) a pneumatic capacitor, said pneumatic capacitor in fluid communication with said primary port.

11. An apparatus as recited in claim 1, further comprising:

(a) a second port, said second port in fluid communication with said chamber; and (b) a pneumatic capacitor, said pneumatic capacitor in fluid communication with said first port, wherein said valve opens and closes by changes in pressure applied to said first port by said pneumatic capacitor.

12. An apparatus as recited in claim 1, wherein said flow pressure applied to said port comprises a patient's airway pressure.

13. A positive pressure pulmonary modulator apparatus, comprising:

(a) a chamber, said chamber including a sleeve;

(b) a port, said port having an interior end and an exterior end, said interior end in flow communication with said chamber;

(c) a valve, said valve engaged within said sleeve and capable of axial movement within said sleeve, said valve including a valve face wherein said valve face has a larger surface area than said interior end of said port, wherein the larger surface area provides a secondary actuation area, wherein said valve is configured to open and close said port by changes in flow pressure applied to said port, and wherein the pressure required to initially move the valve to open the port exceeds the pressure required to be applied to the secondary actuation area to retain the port in an open position; and (d) a biasing member for providing a restorative biasing force on said piston face adjacent to said interior end of said port, wherein said biasing member is configured such that said pressure applied to said port opposes said restorative biasing force.

14. An apparatus as recited in claim 13, further comprising:

(a) a flow restrictor on said chamber, said flow restrictor in flow communication with said port when said valve face is apart from said interior end of said port; and (b) a patient adapter, said patient adapter in fluid connection with said port.

15. An apparatus as recited in claim 13, further comprising means to adjust the amount of bias provided by said biasing member.

16. An apparatus as recited in claim 14, further comprising:

(a) an adapter body;

(b) a connection port, said connection port located on said adapter body, said connection port in fluid communication with said adapter body, said connection port attached to said exterior end of said port of said modulator apparatus;

(c) a gas inlet port, said gas inlet port in fluid communication with said adapter body whereby a compressed gas source can be attached to said patient adapter; and (d) a patient connection port, said patient connection port in fluid communication with said adapter body.

17. An apparatus as recited in claim 16, further comprising:

(a) a one-way flapper valve, said flapper valve in fluid communication with said adapter body, said flapper valve capable of permitting airflow into said adapter body; and (b) means to automatically release gas pressure from within said adapter body.

18. An apparatus as recited in claim 13, wherein said flow pressure applied to said port comprises a patient's airway pressure.

19. A positive pressure aerosol delivery device, comprising:

(a) a pulmonary modulator assembly, said pulmonary modulator assembly comprising:

(i) a chamber, said chamber including a sleeve;

(ii) a port, said port having an interior end and an exterior end, said interior end in flow communication with said chamber;

(iii) a valve, said valve engaged within said sleeve and capable of axial movement within said sleeve, said valve including a valve face wherein said valve face has a larger surface area than said interior end of said port, wherein the larger surface area provides a secondary actuation area, wherein said valve is configured to open and close by changes in flow pressure applied to said port, and wherein the pressure required to initially move the valve to open the port exceeds the pressure required to retain the port in an open position;

(iv) a biasing member that provides a restorative force for biasing said valve face adjacent said interior end of said port, wherein said biasing member is configured such that said pressure applied to said port opposes said restorative force; and (b) a nebulizer assembly, said nebulizer assembly in fluid connection with said port.

20. An apparatus as recited in claim 19, further comprising a flow restrictor on said chamber, said flow restrictor in flow communication with said port when said valve face is apart from said interior end of said port.

21. An apparatus as recited in claim 19, further comprising means to adjust the amount of bias provided by said restoring force means.

22. An apparatus as recited in claim 19, wherein said nebulizer assembly comprises:

(a) a nebulizer chamber and a mouthpiece, said mouthpiece in fluid communication with said nebulizer chamber, said nebulizer chamber in fluid communication with said port of said pulmonary modulator assembly;

(b) a reservoir sealably attached to said nebulizer chamber, said reservoir including a primary orifice, said primary orifice in fluid communication with said nebulizer chamber; and (c) a baffle, said baffle located within said reservoir, said baffle including a secondary orifice, said secondary orifice in fluid communication with said nebulizer chamber.

23. An apparatus as recited in claim 19, wherein said flow pressure applied to said port comprises a patient's airway pressure.

24. A percussive therapy device, comprising:

(a) a pulmonary modulator assembly, said pulmonary modulator assembly comprising:

(i) a chamber, said chamber including a sleeve;

(ii) a first port, said first port having an interior end and an exterior end, said interior end in flow communication with said chamber;

(iii) a second port, said second port in fluid communication with said chamber;

(iv) a modulator valve, said modulator valve engaged within said sleeve and capable of axial movement within said sleeve, said modulator valve including a valve face wherein said modulator valve face has a larger surface area than said interior end of said first port, wherein said modulator valve has dual actuation areas, and wherein flow pressure required to initially move the modulator valve to open the first port exceeds the pressure required to retain the first port in an open position;

(v) a biasing member that provides a restorative force for biasing said valve face adjacent said interior end of said first port, wherein said biasing member is configured such that said pressure applied to said first port opposes said restorative force;

(b) a pneumatic capacitor coupled to said first port, wherein said modulator valve is configured to open and close by changes in said pressure applied to said first port by said pneumatic capacitor; and (c) a patient connection in fluid connection with said second port.

25. An apparatus as recited in claim 24, further comprising a flow restrictor, said flow restrictor in flow communication with said first port when said valve face is apart from said interior end of said first port.

26. An apparatus as recited in claim 24, further comprising means to adjust the amount of bias provided by said biasing member.

27. An apparatus as recited in claim 24, further comprising a nebulizer assembly connected to said second port.

28. An apparatus as recited in claim 27, wherein said nebulizer assembly comprises:

(a) a nebulizer cap, said cap further comprising a nebulizer chamber and a mouthpiece, said mouthpiece in fluid communication with said nebulizer chamber, said nebulizer chamber in fluid communication with said first port of said pulmonary modulator assembly;

(b) a reservoir sealably attached to said cap, said reservoir including a primary orifice, said primary orifice in fluid communication with said nebulizer chamber;

(c) a hemispheric baffle, said baffle located within said reservoir, said baffle including a secondary orifice, said secondary orifice in fluid communication with said nebulizer chamber; and (d) a one-way valve, said valve located within said nebulizer cap, said valve capable of entraining air into said nebulizer chamber.

29. A positive pressure pulmonary apparatus, comprising:

(a) a valve for closing off flow communication with an inlet port to a patient airway, said valve capable of being opened and closed, said valve including a first actuating area capable of fluidly communicating with said patient airway when said valve is closed, said valve including a second actuating area capable of communicating with said patient airway when said valve is open, wherein said first actuating area is of lesser area than said second actuating area, wherein said valve is configured to open and close by changes in flow pressure applied to said inlet port, and wherein the pressure required to be applied to said first actuating area to open said valve is greater than the pressure required to be applied to said second actuating area to hold said valve open;

(b) an outlet port in fluid communication with said inlet port when said valve is open and not in flow communication with said patient airway when said valve is closed; and (c) a biasing member that provides a restorative force acting on said valve to bias said valve toward closure in the absence of a force sufficient to maintain said valve open, wherein said biasing member is configured such that said pressure applied to said inlet port opposes said restorative force.

30. An apparatus as recited in claim 29, wherein said valve closes and inhalation begins at one pressure, thereby inflating a patients lungs while concurrently causing the airway pressure to increase and causing said valve to open and exhalation to begin at a second pressure, and wherein exhaled gases escape through said outlet port.

31. An apparatus as recited in claim 19, further comprising a patient connection port for the attachment of a breathing mask or an endotracheal tube through which a patient may receive gaseous fluids.

32. An apparatus as recited in claim 29, further comprising a gas inlet for attachment of a gas source and delivery of said gas to said apparatus.

33. An apparatus as recited in claim 29, wherein said flow pressure applied to said inlet port comprises a patient's airway pressure.

34. A constant flow, percussive therapy device, comprising:

(a) a valve for closing off flow communication with a pneumatic capacitor, said valve including multiple actuation areas, said valve capable of being opened and closed;

(b) wherein said pneumatic capacitor provides a pressure acting to open said valve, said pneumatic capacitor being in fluid communication with said valve actuation areas, wherein said valve actuation area that is in fluid communication with said pneumatic capacitor is less when said valve is closed than when said valve is open, wherein said valve is configured to open and close by changes in flow pressure applied to said valve actuation areas by said pneumatic capacitor, and wherein the pressure required to be applied by said pneumatic capacitor to open said valve is greater than the pressure required to hold said valve open;

(c) a biasing member that provides a biasing force acting in opposition to said opening pressure wherein said valve closes in the absence of said opening pressure;

(d) a chamber, said chamber located within said pneumatic capacitor;

(e) gas inlet for attachment of a gas source and delivery of gas to said apparatus, said gas inlet in fluid communication with said pneumatic capacitor chamber, said chamber capable of increasing in volume with increases in pressure;

(f) a flow restrictor, said flow restrictor in fluid communication with said pneumatic capacitor when said valve is open and not in fluid communication with said pneumatic capacitor when said valve is closed; and (g) a patient breathing port, said port in fluid communication with said flow restrictor, said port in fluid communication with said chamber when said valve is open.

35. A device as recited in claim 34, further comprising an aerosol producing device, said aerosol producing device in fluid communication with said patient breathing port.

36. A device as recited in claim 35, further comprising an air entrainment valve, said valve in fluid communication with said patient breathing port, said valve providing one way flow to allow gas to enter said percussive therapy device when pressure within said percussive therapy device is less than atmospheric pressure, said valve thereby preventing gas from escaping said percussive therapy device when the pressure within said percussive therapy device exceeds atmospheric pressure.

37. A device as recited in claim 34, wherein said biasing member comprises a spring.

* * * * *